United States Patent [19]

Goodwin et al.

[11] Patent Number: 5,153,132

[45] Date of Patent: * Oct. 6, 1992

[54] THREE-DIMENSIONAL CO-CULTURE PROCESS

[75] Inventors: Thomas J. Goodwin; David A. Wolf, both of Houston, Tex.

[73] Assignee: The United States of America as represented by the Administrator of the National Aeronautics and Space Administration, Washington, D.C.

[*] Notice: The portion of the term of this patent subsequent to Oct. 13, 2009 has been disclaimed.

[21] Appl. No.: 317,931

[22] Filed: Mar. 2, 1989

Related U.S. Application Data

[63] Continuation-in-part of Ser. No. 213,558, Jun. 30, 1988, Pat. No. 5,026,650, and a continuation-in-part of Ser. No. 213,559, Jun. 30, 1988, Pat. No. 4,988,623, and a continuation-in-part of Ser. No. 317,776, Mar. 2, 1989.

[51] Int. Cl.$^5$ .......................... C12N 5/06; C12M 3/02
[52] U.S. Cl. .................................. 435/240.24; 435/3; 435/240.25; 435/286; 435/312
[58] Field of Search .................... 435/3, 289, 240.23, 435/240.24, 240.243, 240.25, 240.2, 174, 176, 177, 283–286, 311, 312

[56] References Cited

U.S. PATENT DOCUMENTS

| | | | |
|---|---|---|---|
| 4,208,483 | 6/1980 | Lee | 435/285 |
| 4,293,654 | 10/1981 | Levine et al. | 435/241 |
| 4,352,887 | 10/1982 | Reid et al. | 435/284 |
| 4,423,145 | 12/1983 | Stampfer et al. | 435/32 |
| 4,605,623 | 8/1986 | Malette et al. | 435/240.23 |
| 4,757,017 | 7/1988 | Cheung | 435/240.24 |
| 4,963,489 | 10/1990 | Naughton et al. | 435/240.23 |
| 4,988,623 | 1/1991 | Schwarz et al. | 435/286 |

FOREIGN PATENT DOCUMENTS

0164888 12/1985 European Pat. Off. ............ 435/286

OTHER PUBLICATIONS

Alberts et al., Molecular Biology of the Cell, New York, Garland Publishing, Inc., 1983, pp. 673–674.
Cherry et al., "Physical Mechanisms of Cell Damage in Microcarrier Cell Culture Bioreactors", Biotech & Bioeng., vol. 32 (1986), pp. 1001–1014.
"The Clinostat-A Tool for Analyzing the Influence of Acceleration on Solid–Liquid Systems", published by the proceedings of a workshop on Space biology, Cologne, Germany, Mar. 11, 1983 (ESASP-206, May 1983). Author: W. Briegleb.
"Large-Scale Cultivation of Mammalian Cells", published in the Scientific American, Jan. 1983, vol. 248, No. 1, pp. 36–43. Authors: Joseph Feder & William R. Tolbert.
"Gravisensitivity of the Acellular, Slime, Mold, Physarum, Polycephalum Demonstrated on the Fast Rotating Clinostat", published in the European Journal of Cell Biology 41, pp. 44–50, 1986. Authors: Ingrid Block & Wolfgang Brigley.
"Cell and Environment Interactions in Tumor Microregions: The Multicell Spheroid Model", Science 240: 177–184, (1988). Author: Robert M. Sutherland.
"Growth and Maintenance of Anchorage Dependent Cells in Zero Headspace Bioreactor Systems Designed for Microgravity", published in the Proceedings Spacebound '87, and presented at a poster session at the First Canadian Workshop on R&D Opportunities on Board the Space Station, National Research Council Canada, May 6–8, 1987. Author: Lewis et al.
"Culture Hepatocytes and Other Differentiated Cells", Hepatology vol. 4 #3, pp. 548–560 (1984). Authors: Lola M. Reid and Douglas M. Jefferson.
"Tissue Culture Model of Adenoma Invasion", Seminars in Surgical Oncology 3:171–173 (1987). Author: Eileen A. Friedman, PhD.

Primary Examiner—Robert J. Warden
Assistant Examiner—William H. Beisner
Attorney, Agent, or Firm—Russell E. Schlorff; Guy M. Miller; Edward K. Fein

[57] ABSTRACT

The process of the present invention relates to a three dimensional co-culture process. Wherein two distinct types of mammalian cells are co-cultured in a rotating bioreactor which is completely filled with culture media and cell attachment substrates. As the size of the tissue assemblies formed on the attachment substrates changes the rotation of the bioreactor is adjusted accordingly.

10 Claims, No Drawings

THREE-DIMENSIONAL CO-CULTURE PROCESS

ORIGIN OF THE INVENTION

The invention described herein was made in the performance of work under NASA contract and is subject to provisions of Section 305 of the National Aeronautics and Space Act of 1958, public Law 85-568 (72 Stat. 435; 42 U.S.C. 2457).

RELATED APPLICATIONS

This application is a continuation-in-part application of U.S. patent applications Ser. No. 7/213,558 filed Jun. 30, 1988 now U.S. Pat. No. 5,026,660 and Ser. No. 7/213,559 filed Jun. 30, 1988, now U.S. Pat. No. 4,988,623 and a U.S. patent application entitled "Three-Dimensional Cell to Tissue Assembly Process" Ser. No. 7/317,776 filed Mar. 2, 1989, all of which are specifically incorporated as if fully set forth herein.

FIELD OF THE INVENTION

The process of the present invention relates to a 3-dimensional coculture process. By the process of the present invention a variety of cells may be co-cultured to produce tissue which has 3-dimensionality and has some of the characteristics of in vivo tissue. The process provides enhanced 3-dimensional tissue which creates a multicellular organoid differentiation model.

BACKGROUND OF THE INVENTION

Cell culture processes have been developed for the growth of single cell bacteria, yeast and molds which are resistant to environmental stresses or are encased with a tough cell wall. Mammalian cell culture, however, is much more complex because such cells are more delicate and have more complex nutrient and other environmental requirements in order to maintain viability and cell growth. Large scale culture of bacterial type cells is highly developed and such culture processes are less demanding and are not as difficult to cultivate as mammalian cells. These techniques are highly empirical and a firm theoretical basis is not developed. Bacterial cells can be grown in large volumes of liquid medium and can be vigorously agitated without any significant damage. Mammalian cells, on the other hand, cannot withstand excessive turbulent action without damage to the cells and must be provided with a complex nutrient medium to support growth.

In addition, mammalian cells have other special requirements, in particular most animal cells must attach themselves to some substrate surface to remain viable and to duplicate. On a small scale, mammalian cells have been grown in containers with small microwells to provide surface anchors for the cells. However, cell culture processes for mammalian cells in such microwell containers generally do not provide sufficient surface area to grow mammalian cells on a sufficiently large scale basis for many commercial or research applications. To provide greater surface areas, microcarrier beads have been developed for providing increased surface areas for the cultured cells to attach. Microcarrier beads with attached cultured cells require agitation in a conventional bio-reactor vessel to provide suspension of the cells, distribution of fresh nutrients, and removal of metabolic waste products. To obtain agitation, such bio-reactor vessels have used internal propellers or movable mechanical agitation devices which are motor driven so that the moving parts within a vessel cause agitation in the fluid medium for the suspension of the microcarrier beads and attached cells. Agitation of mammalian cells, however, subjects them to high degrees of shear stress which can damage the cells and limits ordered assembly of these cells according to cell derived energy. These shear stresses arise when the fluid media has significant relative motion with respect to vessel walls, impellers, or other vessel components. Cells may also be damaged in bio-reactor vessels with internal moving parts if the cells or beads with cells attached collide with one another or vessel components.

In addition to the drawbacks of cell damage, bioreactors and other methods of culturing mammalian cells are also very limited in their ability to provide conditions which allow cells to assemble into tissues which simulate the spatial three-dimensional form of actual tissues in the intact organism. Conventional tissue culture processes limit, for similar reasons, the capacity for cultured tissues to express a highly functionally specialized or differentiated state considered crucial for mammalian cell differentiation and secretion of specialized biologically active molecules of research and pharmaceutical interest. Unlike microorganisms, the cells of higher organisms such as mammals form themselves into high order multicellular tissues. Although the exact mechanisms of this self-assembly are not known, in the cases that have been studied thus far, development of cells into tissues has been found to be dependent on orientation of the cells with respect to each other (the same or different type of cell) or other anchorage substrate and/or the presence or absence of certain substances (factors) such as hormones, autocrines, or paracrines. In summary, no conventional culture process is capable of simultaneously, achieving sufficiently low shear stress, sufficient 3-dimensional spatial freedom, and sufficiently long periods for critical cell interactions (with each other or substrates) to allow excellent modeling of in vivo tissue structure.

Paper entitled "The Clinostat—A Tool For Analyzing The Influence of Acceleration On Solid-Liquid Systems" by W. Brieoleb, was published by the proceedings of a workshop on Space biology, Cologne Germany, on Mar. 11, 1983, (ESASP-206, May 1983). In this paper, clinostat principles are described and analyzed relative to gravity effects. Some clinostat experiments are described including experiments where monocellular suspended organisms (protozoans) are , placed within cylinders which are rotated about a horizontal axis.

A paper entitled, "The Large-Scale Cultivation of Mammalian Cells", by Joseph Feder and William R. Tolbert, was published in the Scientific American, January 1983, Vol. 248, No. 1. pps. 36–43. In this paper, agitation of the cells is described as required to keep the cells suspended in the medium and describes a turbine agitator, a marine propeller agitator, and a vibro mixer for mixing. The paper also describes a perfusion reactor in which an agitation is provided by four slowly rotating flexible sheets of monofilament nylon which are rotated about a vertical axis while the medium in the main vessel is continuously pumped to the satellite filter vessel. The filter retains the cells which are pumped along with the remainder medium back into the vessel for further proliferation.

A paper entitled, "Gravisensitivity of the Acellular, Slime, Mold, Physarum, Polycephalum Demonstrated on the Fast Rotating Clinostat", by Ingrid Block and Wolfgang Brigley, published in the European Journal, of Cell Biology 41, pps. 44–50, 1986 describes rotation of a culture vessel about a horizontal axis for the simulation of weightlessness.

Paper entitled "Cell and Environment Interactions in Tumor Microregions: The Multicell Spheroid Model", by Robert M. Sutherland, Science 240: 177–184, (1988) discloses the use of multicell spheroids, without attachment substrates, of tumor cells to study cell and environment interactions in tumors. Conventional culture processes are utilized to produce limited size and viability tumor cell aggregates.

Cell cultures from various bio-reactors, including a slow turning lateral vessel (STLV) designed for batch culture of cells were presented at a poster session at the First Canadian Workshop on R & D Opportunities on Board the Space Station, National Research Council Canada, May 6-8, 1987, Ottawa, Canada, and published in the Proceedings "Spacebound '87", as a paper entitled "Growth and Maintenance of Anchorage Dependent Cells in Zero Headspace Bioreactor Systems Designed For Microgravity", by Lewis et al.

Paper entitled "Culturing Hepatocyte and other Differentiated Cells", by Lola M. Reid and Douglas M. Jefferson, Hepatology Vol. 4 No. 3 pp 548–560 (1984) discloses limited techniques for the coculturing of hepatocytes and other differentiated cells. The techniques disclosed in the paper make use of floating collagen gels, which are severely restricted in their 3-dimensional aspect and cocultured with fibroblasts moderately to cocultivate differentiated layers of tissue. These techniques do not permit macroscopic inspection of the tissue being cultured as a result of the limited size of the resulting tissue.

Paper entitled "Tissue Culture Model of Adenoma Invasion" by Eileen A. Friedman Seminars in Surgical Oncology 3:171–173 (1987) discloses a model for use of 2-dimensional cocultivation to study the destructive capability of colon carcinoma cells when exposed to normal adenoma cells. This destructive capability is further enhanced by tumor promoters which stimulate the two cell activity.

SUMMARY OF THE INVENTION

The process of the present invention is directed to co-culturing cells to produce multicellular organoid tissue. The process forms and maintains 3-dimensional tissue of such a size as to create a multicellular organoid differentiation model. Combinations of cells of a wide variety may be cultured and maintained so that differentiation and de-differentiation may be studied.

DETAILED DESCRIPTION OF THE INVENTION

The co-culturing process of the present invention optimizes a group of culture environmental conditions, even as the culturing progresses, in a manner which greatly enhances the capability to form and maintain 3-dimensional living tissue from either dissociated source cells or intact tissue resections. The 3-dimensional living tissues are formed and maintained from cells, which is used herein to include cells in any form, for example, individual cells or tissue or dissociated source cells or cells preattached to substrate or intact tissue resections. The process simultaneously minimizes the fluid shear stress, provides 3-dimensional freedom for spatial orientation, and extends localization of cells, tissues, and substrates in a similar spatial region for the duration of the cell culture (collocation). Transient disruptions of this stabilized environment are permitted and well tolerated for logistical purposes during initial system priming, sample acquisition, system maintenance, and culture termination. The cultured 3-dimensional tissues (and substrates) increase in size as the culture progresses necessitating appropriate adjustment of rotational rates with respect to vessel dimensions, external gravitational strength, and absolute sedimentation rate through the media in order to optimize these particle paths. Increased external gravity field strength and increased tissue (and substrate) sedimentation rate induce restrictions on the choice of parameters which ultimately limits the useful operating range of the process. These same factors place a lower limit on the shear stress obtainable even within the process operating range due to gravitationally induced drift of the particles through the culture media. Calculations and measurements place this minimum shear stress very nearly to that resulting from the particles, terminal velocity (through the culture media) for the external gravity field strength Centrifugal and coriolus induced motion along with secondary effects due to particle and fluid interactions act to further degrade the shear stress level as the growing tissue increases in size. 3-dimensionality for spatial orientation of cells, substrates, and tissues is optimized by selecting vessel dimensions and rotational rates which minimize collisions of the cultured particles with vessel walls or internal components. Again, increased gravity and particle sedimentation rate (which is proportional to size in all cases in our experience) cause restrictions to the process operating range in terms of maintaining 3-dimensional freedom. The particular paths which result from rotation of cells, tissues, and substrates about an axis nearly perpendicular to gravity result in these particles, which may differ greatly in sedimentation rates, to remain spatially localized in similar regions for extended periods of time. This allows these particles sufficient time to interact as necessary to form multi-cellular structures and to associate with each other. The ability to retain this spatial approximation of particles, which may differ in sedimentation properties, is degraded by increasing gravity and by increasing particle sedimentation rate. In all three cases minimizing fluid shear stress, maintaining 3-dimensional freedom for spatial orientation, and maximizing spatial approximation of particles with differing sedimentation properties we observe a degradation of performance with increasing external gravitational field strength and with increasing particle sedimentation rate. This then forms the basis for further enhancement of this process in a reduced gravity environment. These three criteria then form the basis for optimization of the culture environment. This process provides the necessary means for support of respiratory gas exchange, supply of nutrients, and removal of metabolic waste products. This is accomplished either by perfusion of media through an external media perfusion loop, direct injection to the culture media, or exchange of these molecules across a diffusion membrane.

This cell and tissue culture process provides a stabilized environment into which cells or tissues may be introduced, suspended, assembled, grown, and maintained with retention of delicate 3-dimensional structural integrity. The fluid culture media is initially stabilized into near solid body horizontal rotation within the confines of a similarly rotating vessel wall. The slowest RPM is chosen which will be sufficient to produce acceptable particle orbits (with respect to the 3 criteria stated in the previous paragraph) upon addition of the initial priming load of cells, tissue, and substrates. In most cases the initial particles with which the culture is primed sediment at a slow rate under 0.1 centimeter per second. It is therefore possible to select from a broad range of rotational rates (typically 5 to 120 RPM) or vessel diameters (typically 0.5 to 36 inches). The slowest rotational rate is advantageous because it minimizes equipment wear and other logistics associated with handling of the culture. A vessel diameter is chosen which has the appropriate volume for the intended quantity of cultured material and which will allow a sufficient seeding density of cells, tissues, and substrates for the availability of these components.

The following is an exemplary protocol for forming and maintaining a multicellular organoid tissue in a slow turning lateral vessel (STLV):

1. An STLV is prepared by tissue culture washing and autoclave sterilization.
2. The sterile, cooled vessel is placed in a Laminar Flow Hood and is stood upright.
3. Average 175 micron microcarrier beads (Cytodex 3 manufactured by Pharmacia) are hydrated and sterilized before hand and diluted into a 20 mg/ml solution of beads in growth media. An appropriate volume of this 20 mg/ml solution is added to the vessel to yield a final bead concentration of 5 mg/ml in the total volume of the vessel.
4. The vessel is filled to all but 10% of the total volume with growth media. The growth media is dependent on the type of cells being cultured in the vessel.
5. The valves are closed and the vessel is placed in a 37° C. humidified $CO_2$ incubator with 95% air 5% $CO_2$ to equilibrate for 1-2 hours. The incubator surrounds the STLV and prevents evaporation of the media from the STLV system.
6. Cell preparation required both mixed normal human colon fibroblasts and human colon tumor cells to be trypsinized from standard culture flasks. The two cell types are mixed together in the correct ratio (9:1) and placed on ice during the wash procedure. After trypsinization the correct cell mixture is washed 2 times with phosphate buffered saline and suspended in the correct growth media. This final cell mixture is held on ice until inoculation.
7. After equilibration and cell preparation the vessel is inoculated with a cell number which will yield 10 cells/bead of the mixed cell ratio. The total number of cells consists of the two cell types (normal human colon fibroblasts and human colon tumor cells). The cell types are mixed in a ratio that promotes cooperative effects seen in the later stages of the coculture process. Each mg of microcarriers contains 4000 beads.
8. After inoculation the vessel is filled to volume with the growth media of choice and placed in the incubator.
9. Initial rotation rates of the vessel are set at 10-15 rpm. These rotation rates suspend the single cells and beads to initiate growth.
10. After 24 hours, the progress of the culture is inspected and a determination is made on the necessity for rotational speed.
11. At 48 hours the first media change usually is made predicated on the metabolism and the cells being cultured. The growth of the culture is monitored by cell counts, glucose, DO2, $DCO_2$ and pH analysis.
12. As the culture develops from 72 hours on, daily adjustments are made in the rotational rate of the vessel dependent on the size of the cell aggregates.
13. Cell and bead aggregates form complex cell masses which are oriented in a three dimensional spatial configuration.
14. Growth limitation occurs as the experiment progresses and increased rotational speed no longer sufficiently suspends the particles. In addition, increased rotational speeds above 35 rpm induce centrifugal forces which smash the particles against the outer wall of the vessel destroying critical three-dimensional spatial orientation.
15. The experiment is terminated when the factors in Item 13 are reached and/or when cellular metabolism in the STLV becomes too demanding to keep up with on a daily basis.

The foregoing protocol of the STLV is only one bioreactor device as a specific example which may be used to carry out the process of, the present invention. As specifically set forth hereinabove the process of co-culturing may be carried out in the rotating wall perfused vessel (RWPV) which is described in the parent application.

EXAMPLE I

A three dimensional multicellular organoid mammalian cell culture was initiated in the following manner. The culture device, a slow turning lateral vessel (STLV), was prepared by washing with a tissue culture detergent, (micro.x) and followed by extensive rinses and soaking in Milli Q ultra high purity water. The device was sterilized by autoclaving and upon cooling was rinsed for residuals with culture growth media. The vessel was placed in a laminar flow hood and stood upright. Cytodex 3 microcarrier beads (Pharmacia) were hydrated and sterilized before hand and suspended in a 20 mg./ml. solution of growth media; each mg. containing 4000 micro carriers. The vessel was filled with the growth media which consisted of minimal essential medium alpha (MEM), supplemented with insulin, transferrin, selenium, (5 ug., 10 ug., 5 ug.), epidermal growth factor, sodium pyruvate, 10% fetal calf serum, hepes buffer 2 grams/liter, and penicillin and streptomycin (100 units, 100 mg./ml.).

62.5 ml. of a 20 mg./ml. solution of microcarriers were added to the vessel to yield a final concentration of 5 mg./ml. of microcarrier in the vessel. The vessel was then filled within 10% of the final volume with growth media. The vessel was sealed and placed in a laminar flow $CO_2$ incubator with 95% air, 5% $CO_2$, 95% humidity at 37° C. to equilibrate for one hour. At the end of one hour, the vessel was removed from the incubator and inoculated with $5 \times 10^7$ cells consisting of mixed normal human colonic fibroblasts (4 donors) and HT-29KM, a partially differentiated human colon adenocarcinoma. The cells were mixed in a (9:1) ratio. After inoculation, the vessel was closed, purged of remaining air bubbles and replaced in the incubator. The vessel was equipped with a 20 ml. syringe which functioned as a compliant volume. Daily monitoring of the growth in the vessel was accomplished by analysis of DCO2, DO2, glucose, mOsm and PH. At 48 hours the growth media was replaced for the first time and each 24-hours thereafter a media change was required. These changes were required to remove toxic metabolic by-products and replenish nutrient levels in the vessel. Media changes were also necessary to harvest rare growth products produced from the interaction of the multicellular organoid culture. On day 2 the rotation rate was increased from 12 to 15 RPM. At 168 hours the media composition was altered to include an additional 100 mg./dl. glucose as a result of increased consumption. At 216 hours the glucose concentration was increased to 300 mg./dl. again due to the high rate of consumption. From 138 hours on the culture exhibited cell to cell organization. At 216 hours the presence of well developed multicellular organoid structures were visible. These structures took on the appearance of circular structures or pseudocrypts. The culture was terminated at 288 hours to begin analysis of the well developed cellular material contained in the vessel. The growth media from the vessel was harvested and placed at $-80°$ C. for future analysis. The cellular material was removed and analyzed for structural components.

The three dimensional multicellular organoid tissue was imbedded in paraffin blocks and cut in 10 and 20 micron sections. These sections were then stained with mucicarmine or hematoxylin and eosin. This histological staining yielded the presence of microscopic cellular organization which was determined to be pseudo-gland formation. In addition, scanning electronmicroscopy showed definite pseudo-crypt formation and the presence of organized tubular structures.

EXAMPLE 2

A three dimensional multicellular organoid mammalian cell culture was initiated in the same manner as described in Example 1.

After removal from the incubator for equilibration, the vessel was inoculated with $5.0 \times 10^7$ cells consisting of mixed normal human colon fibroblasts (4 donors) and HT-29 a pluripotent human adenocarcinoma of the colon. The cell types were mixed in a ratio of (9:1). After inoculation, the vessel was treated as described in Example 1. Daily monitoring was accomplished as stated in Example 1. At 48-hours into the culture the growth media was replaced as in Example 1. The rotation rate was increased on Day 3 from 10 to 14 RPM. At 167 hours into the culture the concentration of glucose in the media was raised from 100 to 200 mg./dl. This was a result of the increased metabolism of the culture. At 264 hours into the culture the growth of the tissues required a second increase in glucose concentration to 300 mg./dl. The run was terminated at 408 hours. As in Example 1 the vessel materials were harvested and processed in a similar fashion.

Upon processing of the tissues from this cell experiment, the multicellular organoid tissues expressed organized polypoid structures.

These polypoid structures were visible both microscopically and macroscopically with the final tissue size approaching 1 cm. Scanning electronmicroscopy revealed an enhanced view of complex polypoid development.

EXAMPLE 3

A three dimensional multicellular organoid mammalian cell culture was initiated in the following manner. The culture device, a rotating wall perfused vessel (500 ml. Volume), was prepared by washing with a tissue culture detergent, (Micro-x) and followed by extensive rinses and soaking in Milli Q water. The device was assembled and then sterilized by Ethylene Oxide gas. After sterilization, the vessel was placed in a laminar flow bench and flushed with mildly acidic ultra pure Milli Q water. At the end of a 16 hour perfusion cycle, the vessel was drained, filled with growth media and allowed to stand overnight at room temperature. The growth media consisted of minimal essential medium alpha (MEM), supplemented with insulin, transferrin, selenium, (5 ug., 10 ug., 5 ug.), epidermal growth factor, sodium pyruvate, 10% fetal calf serum, hepes buffer 2 grams/liter, and penicillin and streptomycin (100 units, 100 mg./ml.). The following day the vessel was drained and refilled with fresh growth media and 2.5 grams of Cytodex 3 micro carriers. The vessel was placed in a $CO_2$ incubator with 95% air, 5% $CO_2$ and 95% humidity to equilibrate for two hours. After equilibration, the vessel was removed from the incubator and inoculated with $1.0 \times 10^8$ cells consisting of mixed normal human colonic fibroblasts (4 donors) and HT-29, a pluripotent human adenocarcinoma of the colon. The cell types were mixed in a (9:1) ratio.

After inoculation the rotating wall perfused vessel was placed in the laminar flow incubator. The vessel was equipped with a 20 ml. syringe which functioned as a compliant volume. The initial wall, vane, and spin filter rotations were set at 18-20 RPM. The perfusion pump was left off for the first 9 hours of the run. At 9 hours into the experiment the pump rate was set at 2.5 ml./min. Daily monitoring of the growth in the vessel was accomplished by analysis of $DCO_2$, $DO_2$, glucose, mOsm and pH. At 48 hours 600 ml. of fresh growth media was perfused into the vessel. This procedure removed any dead or non-attached cells. At 96-hours the vessel was perfused with 600 ml. of fresh growth media to remove toxic metabolic by-products and replenish nutrient levels. At 120-hours the in-line filter became clogged with debris from the rotating seals and the emergency by-pass valve was opened. In addition, 600 ml. of fresh media was also perfused at this time point. At 167 hours into the experiment 600 ml. of 200 mg./dl. glucose growth media was perfused into the vessel.

At 192 hours into the experiment the perfusion pump rate was increased from 2.5 to 4.0 ml./min. and 600 ml. of fresh media was perfused into the vessel. The pump rate was increased to 6 ml./min. at 216 hours and 600 ml. of fresh media was perfused into the system. At 264 hours the pump rate was increased to 9 ml./min. and fresh media (600 ml.) was added to the system. At this point the glucose concentration had to be increased to 300 mg./dl. At 288 hours the pump rate was increased to 10 ml./min. and 600 ml. of 300 mg./dl. glucose was perfused. The pump rate was increased to 11.5 ml./min. at 314 hours and 20 ml. of 50 mg./ml. glucose was added to the system. At 360 hours the pump rate was increased to 13 ml./min. and 600 ml. of 300 mg./dl. glucose growth media was perfused. 600 ml. of 300 mg./dl. glucose media was perfused at 384 hours. The experiment was terminated at 408 hours. From 167 hours into the experiment through to the end the culture exhibited multicellular, structural development. Polypoid formation was evident at first by light microscopy and later macroscopically. The growth media was harvested from the vessel and placed at $-80°$ C. for later analysis. The multicellular tissue material was removed from the vessel and divided into samples for analysis. Analysis of the three dimensional organoid tissue which had been imbedded in paraffin and sectioned, revealed the presence of complex polypoid structures and specific areas of cellular differentiation. These determinations were made by means of mucicarmine and hematoxylin and eosin stains.

We claim:

1. A method for culturing at least two distinct originating types of mammalian cells to produce in vitro multi-cellular, three-dimensional, differentiated, organized, living tissues, said method including the steps of:

providing a bioreactor having a culture chamber rotatable about an approximately horizontal longitudinal axis, means to controllably rotate said culture chamber, means to oxygenate said culture chamber and means to remove metabolic waste products therefrom;

filling said culture chamber completely with a fluid nutrient media, cell attachment substrates, and individually dispersed mammalian cells of at least two distinct types to establish a culturing environment;

rotating said culture chamber about its longitudinal axis, oxygenating the culturing environment within said culture chamber and removing metabolic waste products therefrom;

controlling the rotation of said culture chamber such that the culturing environment except during transient periods has the following simultaneous properties:

a. collocation of cells and attachment substrates with similar or differing sedimentation properties in a similar spatial region, b. freedom for three dimensional spatial orientation of tissues formed by the culturing of the cells, and c. low shear and essentially no relative motion of said culturing environment with respect to the walls of the culture chamber; and determining the trajectory of the tissues, in response to said determining step: increasing the speed of rotation of the culture chamber if the tissues fall excessively inward and downward on the downward side of the rotational cycle and excessively outward and insufficiently upward on the upgoing side of the rotational cycle to prevent wall impact; or decreasing the speed of rotation of the culture chamber in response to excessive accumulation of the tissues near the outer wall of the culture chamber so as not to restrict three dimensional assembly, and as the size of the tissues increase beyond the capability to fully satisfy the above three properties by further increase of the speed of rotation, selecting a rotational rate to visually obtain minimal collision frequency and intensity.

2. The method specified in claim 1 in which one of the cell types are stromal cells and the other cell types are epithelial cells.

3. The method specified in claim 1 in which one of the cell types are fibroblasts and the other cell types are pluripotent human adenocarcinoma.

4. The method specified in claim 1 in which one of the cell types are normal human colon fibroblasts and the other cell types are human colon tumor cells.

5. The method specified in claim 4 in which the fibroblasts and tumor cells are at a 9:1 ratio.

6. The method of claim 1 wherein the vessel is located in microgravity.

7. The method of claim 1 wherein the vessel is located in unit gravity.

8. The method of claim 7 wherein the vessel is rotated within the range of 5 and 25 RPM, and the RPM is increased as the density of the assembly increases.

9. The method of claim 1 wherein the method of sustaining said media is by perfusion.

10. The method of claim 1 wherein the cell attachment substrates are microcarrier beads.

* * * * *